United States Patent [19]
Yoshida

[11] Patent Number: 5,882,301
[45] Date of Patent: Mar. 16, 1999

[54] MEASURING APPARATUS FOR INTRAOCULAR SUBSTANCE EMPLOYING LIGHT FROM EYEBALL

[76] Inventor: Akitoshi Yoshida, 5-8, 6-chome, Kaguraoka 4-jo, Asahikawa-shi, Hokkaido 078, Japan

[21] Appl. No.: 766,222

[22] Filed: Dec. 12, 1996

[30] Foreign Application Priority Data

Dec. 13, 1995 [JP] Japan ................................. 7-347199

[51] Int. Cl.⁶ ..................................................... A61B 5/00
[52] U.S. Cl. .......................................... 600/318; 600/319
[58] Field of Search ................................. 600/310, 318, 600/319, 320, 321, 473, 476

[56] References Cited

U.S. PATENT DOCUMENTS

| | | | |
|---|---|---|---|
| 4,412,543 | 11/1983 | Vassilliadis et al. | 600/321 |
| 4,838,679 | 6/1989 | Bille . | |
| 4,852,987 | 8/1989 | Lohmann . | |
| 5,025,785 | 6/1991 | Weiss | 600/318 |
| 5,202,708 | 4/1993 | Sasaki et al. . | |
| 5,243,983 | 9/1993 | Tarr et al. | 600/318 |
| 5,308,919 | 5/1994 | Minnich | 600/320 |
| 5,433,197 | 7/1995 | Stark | 600/319 |
| 5,435,309 | 7/1995 | Thomas et al. | 600/310 |
| 5,535,743 | 7/1996 | Backhaus et al. . | |
| 5,553,617 | 9/1996 | Barkenhagen | 600/321 |

FOREIGN PATENT DOCUMENTS

| | | |
|---|---|---|
| 167877A2 | 1/1986 | European Pat. Off. . |
| 261957A1 | 11/1988 | Germany . |
| 4243142A1 | 6/1994 | Germany . |
| WO87/03188 | 6/1987 | WIPO . |

OTHER PUBLICATIONS

"A Scanning Ocular Spectrofluorophotometer," McLaren et al., Investigative Ophthalmology & Visual Science, vol. 29, No. 8, Aug. 1988, pp. 1285–1293.

*Primary Examiner*—Michael Peffley
*Assistant Examiner*—Bryan K. Yarnell
*Attorney, Agent, or Firm*—Nikaido, Marmelstein, Murray and Oram

[57] ABSTRACT

Relative directions of excitation and photoreceiving optical systems are so set that an angle formed by optical axes thereof in the air is 14°, and an eyeball is fixed in such a direction that its ocular axis divides the angle formed by the optical axes into two equal parts. On a light incidence side of a one-dimensional solid-state image pickup device of the photoreceiving optical system, a slit is arranged for inputting measuring light components generated from portions of the eyeball having different depth positions on an excitation light beam in photoelectric conversion elements of different positions of the image pickup device. The measuring light components generated from the respective portions of the eyeball parallel to the optical axis are incident upon the one-dimensional solid-state image pickup device through the slit and simultaneously detected, so that the positions of the photoelectric conversion elements and measuring light component generating positions at the eyeball correspond to each other.

46 Claims, 14 Drawing Sheets

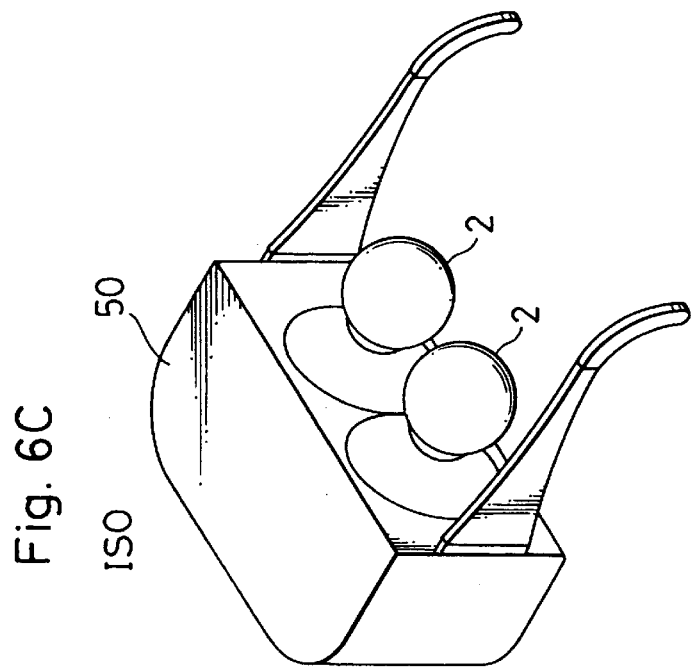
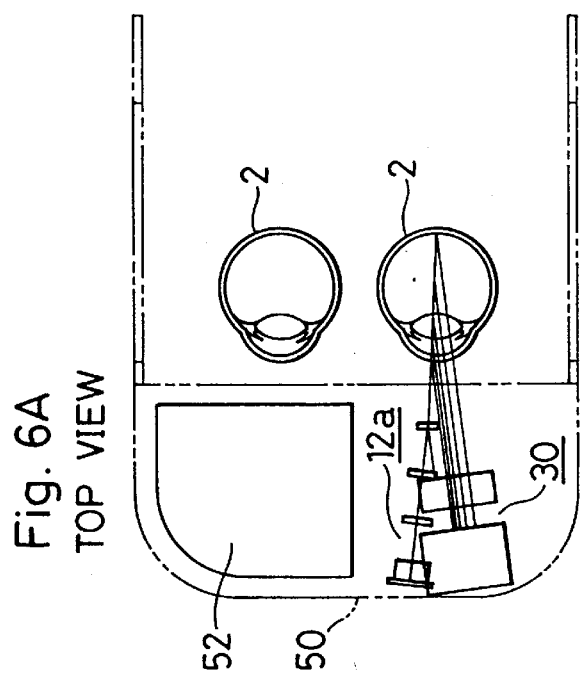
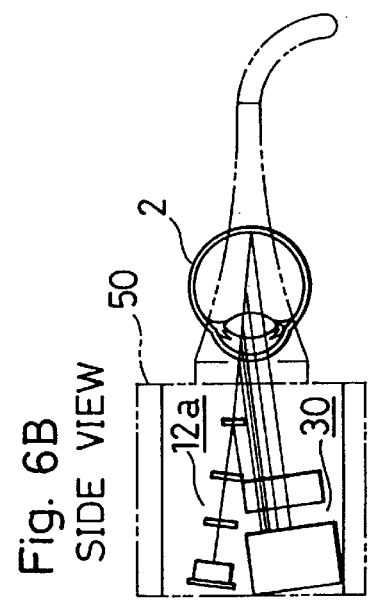

MEASURING APPARATUS FOR INTRAOCULAR SUBSTANCE EMPLOYING LIGHT FROM EYEBALL

BACKGROUND OF THE INVENTION

1. Field of the Invention

The present invention relates to an apparatus for measuring intraocular substances by irradiating an eyeball with an excitation light beam from an excitation optical system and detecting measuring light components including at least either scattered light or fluorescence generated from the eyeball by a photoreceiving optical system.

2. Description of the Background Art

Vitreous fluorophotometry (VFP) is performed as an examination of quantitatively testing the function of a blood-ocular barrier by measuring intraocular fluorescence as a method of irradiating the eyeball with excitation light and obtaining information from scattered light or fluorescence from the eyeball.

In order to diagnose diabetes mellitus or judge necessity for insulin administration, blood-sugar level must be measured. Although a method of collecting blood for measuring the blood-sugar level is correct, this causes the patient pain, and the examination is troublesome and requires a long time.

Therefore, various methods of noninvasively measuring intraocular substances on the basis of optical information from eyeballs are studied. For example, methods of irradiating eyeballs with excitation light and measuring the blood-sugar levels on the basis of information obtained therefrom are studied. One of such methods is a method of irradiating the crystalline lens with excitation light, receiving back-scattered light thereof, separating the same into fluorescence and Rayleigh light through a spectroscope or a dichroic beam splitter, obtaining information allowing diagnosis of diabetes mellitus from a value obtained by normalizing the fluorescence intensity with the Rayleigh light intensity, and diagnosing diabetes mellitus, cataract or still another disease on the basis thereof (refer to U.S. Pat. No. 5,203,328).

In another method, infrared absorption by the crystalline lens or the refractive index of visible light is measured for obtaining the blood-sugar level in the crystalline lens on the basis thereof (refer to Japanese Patent Laying-Open Gazette No. 51-75498 (1976)). In still another method, aqueous humor filling up a clearance between the cornea and the crystalline lens is irradiated with plane polarized light so that the blood-sugar level is obtained by measuring the angle of rotation of the polarization axis or the refractive index (refer to U.S. Pat. No. 3,963,019).

A method of obtaining a cholesterol value as another vital substance is also proposed. In this method, aqueous humor is irradiated with excitation light, so that the intensity of scattered light therefrom or the mobility of protein which is a scatterer is measured for obtaining the cholesterol value (refer to U.S. Pat. No. 4,836,207).

Obtained information varies with the measured eyeball portion such as the vitreous body, the crystalline lens, the aqueous humor or the cornea. In order to obtain information from positions of the eyeball having different depths, therefore, an optical system is so scanned that places for generating fluorescence etc. to be received move along the depth direction of the eyeball (refer to "Ringan" Vol. 38, No. 11, 1195–1199 (1984)).

When the optical system is scanned for measurement for obtaining information from eyeball positions having different depths and the eyeball moves during the scanning, the depths of the measured portions are also changed and no correct measurement can be performed.

Further, the optical system is disadvantageously complicated and increased in size due to the scanning.

SUMMARY OF THE INVENTION

Objects of the present invention are to simplify measurement by making it possible to simultaneously detect light components generated from a plurality of eyeball portions having different depths, to make scanning of an optical system unnecessary, and to miniaturize a measuring apparatus.

A measuring apparatus according to the present invention is adapted to irradiate an eyeball with a monochromated or single-wavelength excitation light beam of visible to near infrared regions from an excitation optical system for detecting measuring light components including at least either scattered light or fluorescence generated from the eyeball by a photoreceiving optical system, thereby measuring intraocular substances. Optical axes of the excitation and photoreceiving optical systems are spatially different from each other, and so arranged as to intersect with each other in the eyeball without striking the iris in a state of fixing the ocular axis in a proper direction for measurement, i.e., in a fixation state, while the photoreceiving optical system comprises an optical element for guiding measuring light components generated along the excitation light beam in eyeball positions having different depths to positions associated with the measuring light component generating positions, and a photodetector for detecting the measuring light components guided by the optical element.

Preferably, the photoreceiving optical system further comprises spectroscopic means for separating the measuring light components generated from the eyeball into spectral components. The spectroscopic means is provided between the optical element and the photodetector, which in turn is arranged to detect the measuring light components separated into the spectral components by the spectroscopic means. The spectroscopic means can alternatively be arranged on a light incidence side of the optical element, if the same is not of a wavelength dispersion type.

A first example of the optical element is a spatial aperture consisting of a slit formed by arranging a plurality of thin plates which are parallel to the optical axis of the photoreceiving optical system, or an optical fiber lens array formed by arranging optical fiber lenses in parallel with the optical axis of the photoreceiving optical system. A second example of the optical element is a conjugate optical system including a lens, which is adapted to form images of the measuring light component generating positions in the eyeball along the excitation light beam on the photodetector or the spectroscopic means.

According to a preferred aspect of the present invention, the photodetector is prepared from a one-demensional solid-state image pickup device such as a CCD sensor or a photodiode array having a plurality of photoelectric conversion elements which are arranged along a straight line having a constant angle with respect to the optical axis of the photoreceiving optical system in a plane including the optical axes of the excitation and photoreceiving optical systems. In this case, the spectroscopic means is prepared from a Fourier transform spectroscope (FT), a filter or an acousto-optic tunable filter (AOTF), and the optical element associates the positions of the photoelectric conversion elements of the one- dimensional solid-state image pickup device with the measuring light component generating positions in the eyeball along the excitation light beam.

According to another preferred aspect of the present invention, the photodetector is prepared from a two-dimensional solid-state image pickup device such as a CCD image pickup device having a plurality of two-dimensionally arranged photoelectric conversion elements, the spectroscopic means is a diffraction grating, the optical element associates the positions of the photoelectric conversion elements in a line of photoelectric conversion element arrangement in the two-dimensional solid-state image pickup device with the measuring light component generating positions in the eyeball along the excitation light beam, and the photoreceiving optical system structures a multi-channel spectroscope for wavelength- dispersing the measuring light components from the respective positions in a direction perpendicular to the photoelectric conversion element arrangement and simultaneously detecting the same.

When the photodetector is prepared from a two-dimensional solid-state image pickup device, the excitation optical system can further comprise a beam sweep mechanism for moving the excitation light beam in the direction perpendicular to the plane including the optical axes of the excitation and photoreceiving optical systems. In this case, two-dimensional information in the eyeball can be obtained.

The excitation light beam applied to the eyeball from the excitation optical system, which is a monochromated or single-wavelength beam in visible to near infrared regions, is preferably a parallel beam along the optical axis of the excitation optical system. An exemplary excitation optical system for generating such an excitation light beam comprises a light source of an incandescent lamp such as a tungsten lamp or a halogen lamp for generating excitation light of a continuous wavelength, wavelength selection means such as a filter for monochromating the light from the light source, and a slit for converting the excitation light to a parallel beam along the optical axis of the excitation optical system.

Another exemplary excitation optical system comprises a laser unit for generating excitation light of a single wavelength in visible to near infrared regions as a light source. When the laser unit is prepared from a semiconductor laser unit, the beam diverges and hence a lens or a slit is necessary for converting the excitation light to a parallel beam along the optical axis of the excitation optical system. When the semiconductor laser unit oscillates a plurality of wavelength light components, wavelength selection means such as an optical filter is necessary for selecting a specific wavelength light component.

When Raman scattered light or fluorescence is received, data processing is simplified if the excitation light beam is monochromatic or single-wavelength light. When the excitation light is converted to a parallel beam, it is convenient in performance of area integration.

When a beam splitter is provided on an optical axis of the excitation light beam of the excitation optical system so that part of the excitation light extracted by the beam splitter is incident upon partial photoelectric conversion elements and outputs of the photodetector receiving the measuring light components from the eyeball are corrected by outputs of the photoelectric conversion elements, the scattered light or the fluorescence can be correctly measured even if the excitation light fluctuates.

Preferably, the apparatus is further provided with an ocular axis fixing optical system comprising an ocular axis fixing light source for generating visible light independently of the light source of the excitation optical system for introducing a light beam from this light source into the eyeball, in order to fix the ocular axis in a specific direction, e.g., the optical axis direction of the photoreceiving optical system, or to maintain a constant angle with the optical axis direction, in measurement.

The ocular axis fixing optical system may be provided on the side of either the eyeball employed for measuring the intraocular substances or another eyeball not employed for the measurement.

If the ocular axis is not fixed, it is preferable that the measurement can be made when the ocular axis is in a prescribed direction suitable for the measurement. To this end, a two-dimensional solid-state image pickup device such as a CCD solid-state image pickup device may be provided as a monitor for monitoring the eyeball direction so that information such as the eyeball direction, the position of incidence of the excitation light beam and the like can be incorporated by the two-dimensional solid-state image pickup device. The two-dimensional solid-state image pickup device for monitoring can also be provided on the side of either the measuring eyeball or another eyeball.

The excitation and photoreceiving optical systems can be integrally stored in a goggle structure which can be attached to the face, so that the measurement can be readily performed.

This goggle structure can further be provided with a transmission circuit which can output information including data measured by the photoreceiving optical system to an external data processor. The transmission circuit for transmitting the measured data can be implemented by any means such as wireless, wire or optical pulse means.

The first measured intraocular substance is sugar, and determination can be made for glucose through a Raman scattering peak at 420 to 1500 $cm^{-1}$ or 2850 to 3000 $cm^{-1}$, preferably at 420 to 450 $cm^{-1}$, 460 to 550 $cm^{-1}$, 750 to 800 $cm^{-1}$, 850 to 940 $cm^{-1}$, 1000 to 1090 $cm^{-1}$, 1090 to 1170 $cm^{-1}$, 1200 to 1300 $cm^{-1}$, 1300 to 1390 $cm^{-1}$, 1450 to 1500 $cm^{-1}$ or 2850 to 3000 $cm^{-1}$ in a shift wavenumber from an excitation wavelength. Glucose (grape sugar), which is also called blood sugar, gives most important information for diagnosing diabetes mellitus or recognizing transition of the condition of a disease.

Another sugar can also be measured. With respect to inositol, for example, determination can be made through a Raman scattering peak at 400 to 1500 $cm^{-1}$ or 2900 to 3050 $cm^{-1}$, preferably at 400 to 500 $cm^{-1}$, 700 to 900 $cm^{-1}$, 1000 to 1100 $cm^{-1}$, 1200 to 1500 $cm^{-1}$ or 2900 to 3050 $cm^{-1}$ in a shift wavenumber from the excitation wavelength.

With respect to fructose, determination can be made through a Raman scattering peak at 550 to 1500 $cm^{-1}$ or 2900 to 3050 $cm^{-1}$, preferably at 550 to 620 $cm^{-1}$, 650 to 700 $cm^{-1}$, 780 to 870 $cm^{-1}$, 900 to 980 $cm^{-1}$, 1000 to 1150 $cm^{-1}$, 1200 to 1300 $cm^{-1}$, 1400 to 1480 $cm^{-1}$ or 2900 to 3050 $cm^{-1}$ in a shift wavenumber from the excitation wavelength.

With respect to galactose, determination can be made through a Raman scattering peak at 400 to 1500 $cm^{-1}$ or 2850 to 3050 $cm^{-1}$, preferably at 450 to 550 $cm^{-1}$, 630 to 900 $cm^{-1}$, 1000 to 1180 $cm^{-1}$, 1200 to 1290 $cm^{-1}$, 1300 to 1380 $cm^{-1}$, 1400 to 1500 $cm^{-1}$ or 2850 to 3050 $cm^{-1}$ in a shift wavenumber from the excitation wavelength.

With respect to sorbitol, determination can be made through a Raman scattering peak at 380 to 1500 $cm^{-1}$ or 2700 to 2960 $cm^{-1}$, preferably at 388 to 488 $cm^{-1}$, 749 to 862 $cm^{-1}$, 933 to 1120 $cm^{-1}$, 1380 to 1464 $cm^{-1}$ or 2731 to 2960 $cm^{-1}$ in a shift wavenumber from the excitation wavelength.

The second measured intraocular substance is lipid, and determination can be made through a spectral intensity of a fluorescent spectrum of 450 to 650 nm or an integrated value of a spectrum in a proper wavelength range within the range with respect to lecithin (phosphatidylcholine).

The third measured intraocular substance is bilirubin, and determination can be made through a Raman scattering peak at at 500 to 540 $cm^{-1}$, 670 to 710 $cm^{-1}$, 900 to 980 $cm^{-1}$, 1220 to 1300 $cm^{-1}$, 1310 to 1330 $cm^{-1}$, 1400 to 1500 $cm^{-1}$ or 1550 to 1670 $cm^{-1}$ in a shift wavenumber from the excitation wavelength.

The fourth measured intraocular substance is glycated protein, and determination can be made through a spectral intensity of a fluorescent spectrum of 640 to 850 nm or an integrated value of a spectrum in a proper wavelength range within the range with respect to glycated albumin.

The fifth measured intraocular substance is an AGE (advanced glycated end product). The AGE can also be similarly measured and determined. The AGE, called a late stage product, is a product in a late stage of such nonenzymic saccharification reaction (glycation) that an amino group of amino acid, peptide or protein reacts with a carbonyl group of reducing sugar, and watched as a substance related to organopathy resulting from a diabetic chronic complication.

The sixth measured intraocular substance is saccharified crystallin. Saccharified crystallin can also be similarly measured and determined.

These intraocular substances are substances which are present in the body. A conventional method of measuring fluorescence from an eyeball is performed after injecting fluorescein-Na into a vein. The present invention can also be utilized as an apparatus for measuring such an externally injected fluorescent substance. To this end, the seventh measured intraocular substance is an externally injected fluorescent substance such as fluorescein-Na.

When the measured intraocular substances are at least two types of substances among sugar, lipid, bilirubin, glycated protein, an AGE, saccharified crystallin and the like, peak intensities or peak areas of Raman scattered light components of shift wavenumbers selected for these substances, spectral intensities of fluorescence, or integrated values of proper wavelength ranges are employed, so that measured values of the respective substances can be obtained from these plurality of measured values by multivariate regression analysis.

The multivariate regression analysis operation is adapted to make data analysis through multivariate regression analysis such as principal component regression analysis (PCR) or a partial least square method (PLS method). In the multivariate regression analysis, regression analysis can be made by employing a number of spectral intensities at once, whereby quantitative analysis of higher accuracy as compared with single regression analysis is possible. While multiple regression analysis is most generally employed, a number of samples are required and its quantitative analysis accuracy is reduced if correlation between spectral intensities at respective shift wavenumbers is high. On the other hand, PCR which is multivariate regression analysis can intensify spectral intensities at a plurality of shift wavenumber regions to principal components which are irrelevant to each other and delete unnecessary noise data, whereby high quantitative analysis accuracy can be attained. Further, the PLS method can also utilize data of sample concentration in extraction of principal components, whereby high quantitative analysis accuracy can be attained similarly to the PCR. As to the multivariate regression analysis, "Tahenryo Kaiseki" (by Kazuo Nakatani, Shinyo-Sha) can be referred to.

In order to draw out necessary information from a spectrum complexity fluctuating by various fluctuation factors, data processing by a computer is remarkably useful. A typical processing method is stored in processing software provided in a commercially available near infrared apparatus or the like. As commercially available software, there is Unscramber by CAMO Company or the like. The typical processing method is the aforementioned multiple regression analysis, PLS, the principal component regression analysis or the like.

Large streams of data processing which is applied to quantitative regression analysis by multivariate regression analysis are (1) formation of a calibration model (calibration curve), (2) evaluation of the calibration model, and (3) determination of an unknown sample.

In order to perform calibration, it is necessary to measure a proper number of samples for forming a calibration curve in sufficient accuracy. Obtained spectra are subjected to preprocesses at need. Typical preprocesses are smoothing, differentiation and normalization of the spectra, which are general processes.

The calibration is processing of constructing mathematical relational expressions between spectral data and analytical values of target characteristics, i.e., models. Formation of models is performed by a statistical technique by employing analytical values of samples for forming a calibration curve and spectral data.

In order to correctly evaluate accuracy of prediction of the prepared calibration curve with respect to an unknown sample, measurement errors with respect to the unknown sample are obtained through an evaluation sample. When the accuracy of the calibration curve is decided as being insufficient, the type of the processing method or parameters are changed at need, to correct the calibration curve.

A calibration curve which is recognized as having sufficient accuracy is employed as a relational expression for predicting values of target characteristics from spectral data in analysis of the unknown sample, to be used for determination of the unknown sample concentration.

According to the present invention, the eyeball is irradiated with the excitation light beam from the excitation optical system so that the photoreceiving optical system simultaneously detects measuring light components including at least either scattered light or fluorescence generated from a plurality of eyeball positions having different depths while the measuring light component generating positions of the eyeball having different positions are associated with the positions of the photoelectric conversion elements of the photodetector of the photoreceiving optical system, whereby information can be noninvasively and simultaneously obtained from the plurality of eyeball positions having different depths. Therefore, it is possible to eliminate such an inconvenience that the eyeball moves during the measurement to disable the measurement, dissimilarly to the conventional case of making scanning in the depth direction of the eyeball.

Further, no scanning mechanism is necessary for the optical systems, whereby the optical systems can be miniaturized and integrated into a goggle structure, to be easy to handle.

Thus, an operation of obtaining optical information from the eyeball portions having different depths for measuring intraocular substances in each part is simplified, and information useful for diagnosis of a disease such as diabetes mellitus can be noninvasively obtained.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 2A and 3B are schematic plan sectional views showing optical elements prepared from an optical fiber lens array and a lens respectively for substituting for slits in the first and second embodiments;

FIGS. 6A, 6B and 6C are a plan view showing arrangement of internal optical systems integrated into a goggle structure, a side elevational view on a photoreceiving optical system side showing the arrangement of the internal optical systems, and a perspective view as viewed from an eyeball side respectively;

DESCRIPTION OF THE PREFERRED EMBODIMENTS

Figure 1:
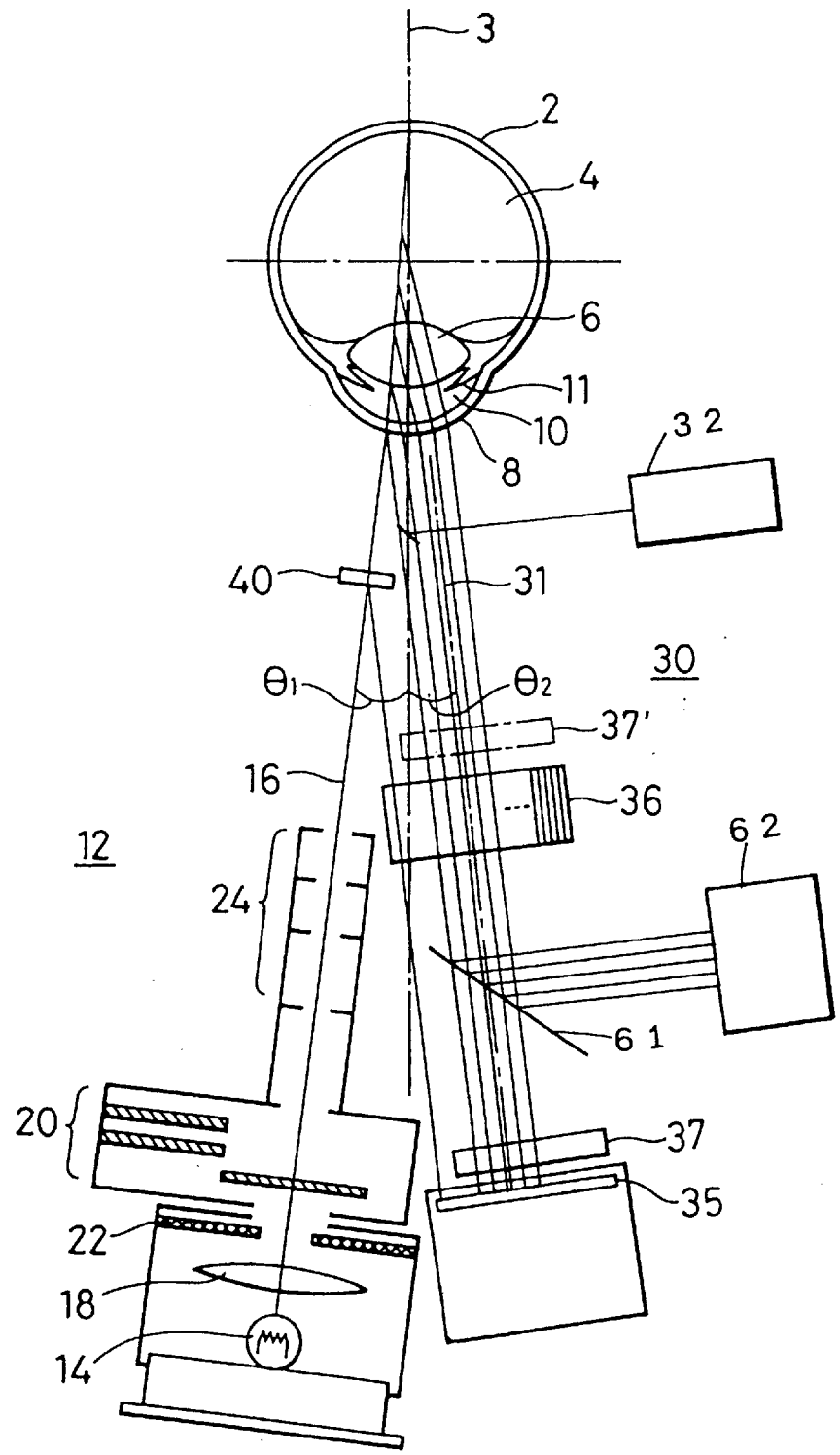
FIG. 1 is a schematic plan sectional view showing a first embodiment of the present invention.

FIG. 1 schematically illustrates a first embodiment of the present invention. Numeral 2 denotes an eyeball, which is provided with a vitreous body 4, a crystalline lens 6 provided in front of the vitreous body 4, and a cornea 8 provided at the frontmost portion. A clearance between the cornea 8 and the crystalline lens 6 is filled with aqueous humor 10, which is a transparent liquid. An iris 11 is provided between the crystalline lens 6 and the cornea 8, with a pupil on its central opening. Numeral 3 denotes an ocular axis.

An excitation optical system 12 comprises an incandescent lamp such as a tungsten lamp as a light source 14, and a lens 18 for condensing excitation light generated from the light source 14 and optical filters 20 for extracting a narrow wavelength range from the excitation light and monochromating the same are provided on an optical axis 16 of the excitation optical system 12. A plurality of, three in the shown embodiment, optical filters 20 are provided to be switchable in response to a desired excitation light beam wavelength. The excitation light beam is adjusted to a narrow parallel beam of 0.1 to 2 mm in diameter through a slit 22 provided between the optical filters 20 and the lens 18 and a plurality of slits 24 closer to an outgoing side than the optical filters 20.

A photoreceiving optical system 30 has an optical axis 31 which is spatially different from the optical axis 16 of the excitation optical system 12, and relative directions of the optical systems 12 and 30 are so set that an angle formed by the optical axes 16 and 31 of the excitation and photoreceiving optical systems 12 and 30 in the air is 14°. The ocular axis 3 of the eyeball 2 is fixed in a direction dividing the angle formed by the optical axes 16 and 31 into two equal parts, and measured. In this state, the optical axes 16 and 31 are positioned on opposite sides, and both of angles $\theta_1$ and $\theta_2$ formed by the optical axes 16 and 31 and the ocular axis 3 are 7°.

The photoreceiving optical system 30 has a one-dimensional solid-state image pickup device 35 such as a CCD sensor or a photodiode array which is arranged on its optical axis 31 as a photodetector. The one-dimensional solid-state image pickup device 35 comprises CCD photoelectric conversion element arrangement arranged in a line in a direction along a straight line perpendicular to the optical axis 31 in a plane including the optical axes 16 and 31. The photoelectric conversion element arrangement of the one-dimensional solid-state image pickup device 35 is at pitches of 125 $\mu$m, for example.

A slit 36 is arranged on a light incidence side of the one-dimensional solid-state image pickup device 35 as an optical element for inputting measuring light components generated from portions of the eyeball 2 having different depth positions on the excitation light beam in the photoelectric conversion elements of the photodetector 35 at different positions. The slit 36 is prepared by arranging a plurality of thin plates which are in a direction parallel to the optical axis 31 and perpendicular to the plane including the optical axes 16 and 31 in a direction perpendicular to the optical axis 31 in the plane including the optical axes 16 and 31. The slit 36 preferably has pitches corresponding to the photoelectric conversion element pitches of the one-dimensional solid- state image pickup device 35, and its depth is 5 to 30 mm.

Spectroscopic means 37 such as an FT, a filter or an AOTF is arranged between the slit 36 and the one-dimensional solid-state image pickup device 35, to be capable of separating the measuring light components from the eyeball 2 into spectral components. The spectroscopic means 37 such as an FT, a filter or an AOTF may alternatively be arranged on a measuring light component incidence side for the slit 36, as denoted by numeral 37'.

In order to fix the ocular axis 3 in the fixed direction, an optical system 32 comprising a light source for generating visible light, a slit for converting light from the light source to a narrow beam, and a half mirror for placing the beam adjusted by the slit on the optical axis 31 and introducing the same into the eyeball 2 is further provided in the photoreceiving optical system 30.

In order to incorporate information including a direction of the eyeball 2 and a position of incidence of the excitation light beam, the photoreceiving optical system 30 is further provided with a half mirror 61 on the optical axis 31 and CCD image pickup device 62 to receive a light from the eyeball 2 extracted by the half mirror 61 for monitoring the orientation of the eyeball 2.

In order to correct fluctuation of the light source intensity a half mirror 40 is arranged on the optical axis 16 of the excitation optical system 12, so that parts of the excitation light are directly incident upon partial photoelectric conversion elements of the one-dimensional solid-state image pickup device 35. Detection signals from respective parts of the eyeball 2 received by the remaining photoelectric conversion elements of the one-dimensional solid-state image pickup device 35 are divided by detection signals of the partial photoelectric conversion elements receiving the parts of the excitation light and normalized, so that fluctuation of the light source intensity is correctly measured and correct measured values can be obtained.

The operation of the embodiment shown in FIG. 1 is now described. The excitation light beam is incident upon the cornea 8, and reaches the retina through the aqueous humor 10, the crystalline lens 6 and the vitreous body 4. Respective parts of the eyeball 2 are irradiated with the excitation light beam, and only components, parallel to the optical axis 31, of the measuring light components of scattered light and fluorescence generated from the respective parts are separated into spectral components by the slit 36 through the spectroscopic means 37 and incident upon the one-dimensional solid-state image pickup device 35. Due to the provision of the slit 36, the position of the photoelectric conversion elements of the one-dimensional solid-state image pickup device 35 correspond to the measuring light component generating positions of the eyeball 2, whereby it is possible to identify from which depth positions the data are generated.

In case of employing a two-dimensional solid-state image pickup device as the photodetector, a multi-channel spectroscope can be employed as the spectroscopic means 37. In this case, a line of measuring light components incident upon the spectroscope through the corresponding slit 36 correspond to the positions in the eyeball 2. Due to wavelength dispersion in a direction perpendicular to the direction of arrangement of the measuring light components incident upon the spectroscope, it is possible to simultaneously separate measuring light components from a plurality of positions in the eyeball 2 into spectral components and to simultaneously detect the same over respective multi-wavelengths.

Figure 2:
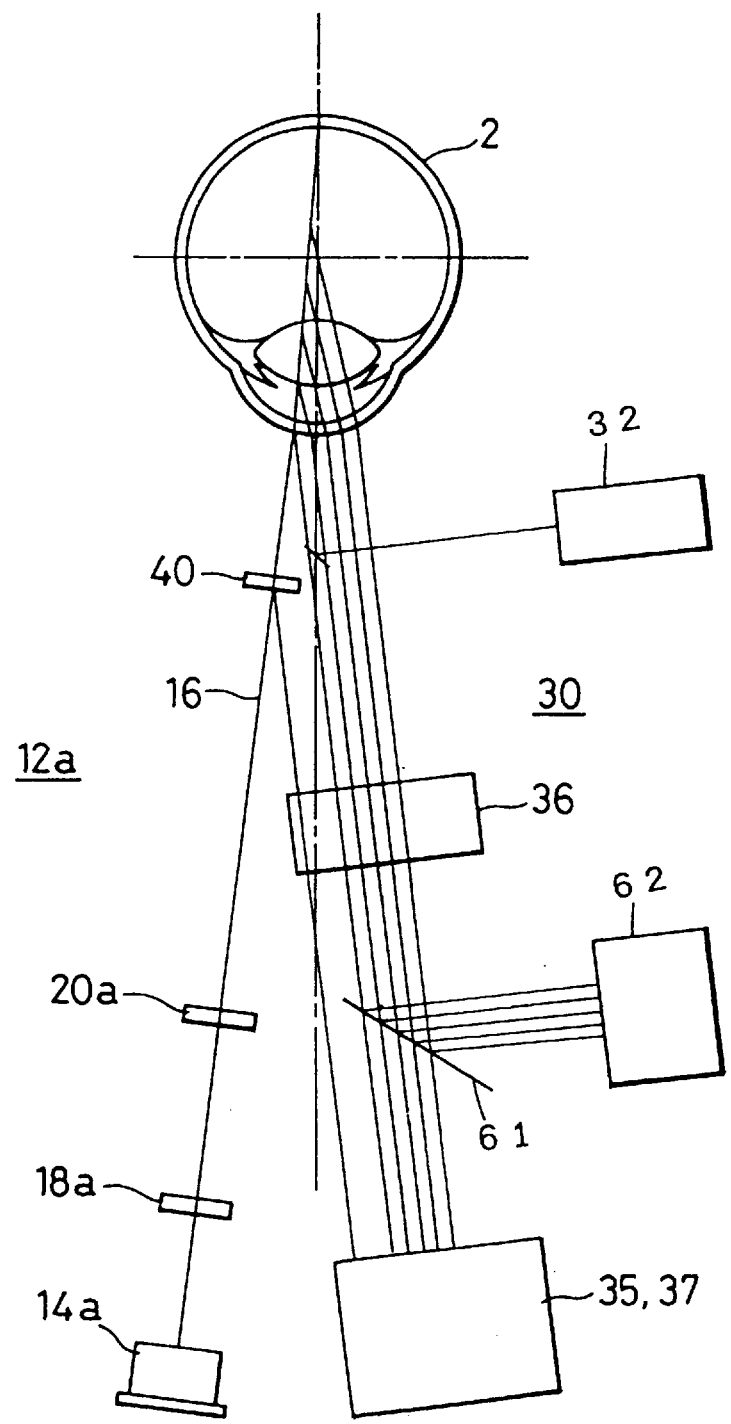
FIG. 2 is a schematic plan sectional view showing a second embodiment of the present invention.

FIG. 2 illustrates an embodiment employing a semiconductor laser unit 14a as a light source of an excitation optical system 12a. The semiconductor laser unit 14a is arranged on an optical axis 16 of the excitation optical system 12a as a light source, while a lens 18a for converting an excitation light beam to a parallel beam on the optical axis 16 and an optical filter 20a for selecting specific wavelength light are arranged on a light emitting side of the semiconductor laser unit 14a on the optical axis 16. The remaining structure and the operation are identical to those of FIG. 1.

Figure 3A:
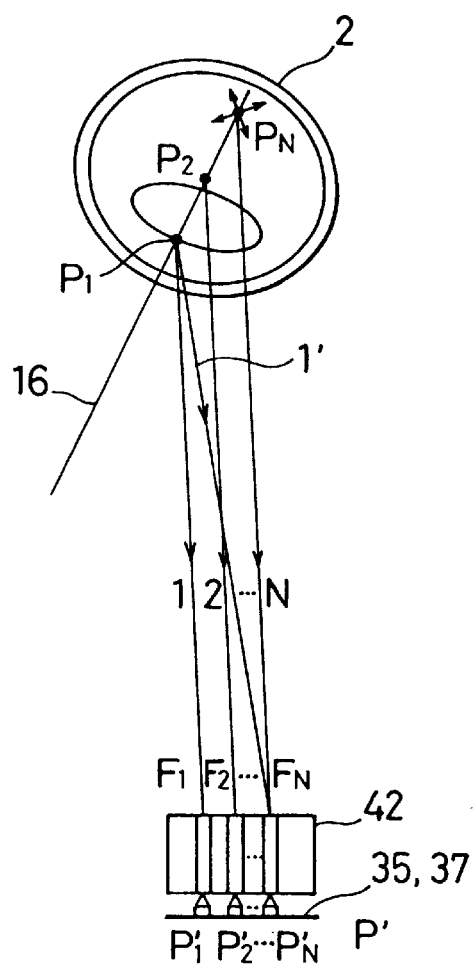
Figure 3B:
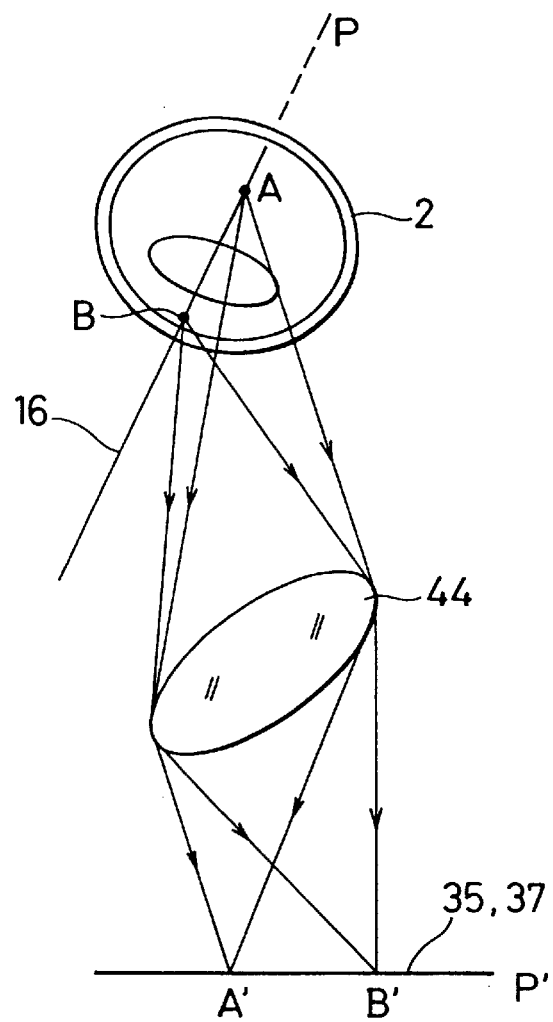

FIGS. 3A and 3B illustrate exemplary optical elements for associating eyeball portions having different depths for generating measuring light components with positions of photoelectric conversion elements of photodetectors in place of the slit 36 shown in FIG. 1. FIG. 3A shows an optical element employing an optical fiber lens array 42, having optical fiber lenses preferably at pitches corresponding to those of photoelectric conversion elements of a one-dimensional solid-state image pickup device 35. Measuring light components generated from respective portions $P_1$ to $P_N$ of an eyeball irradiated with an excitation light beam are selected by respective optical fiber lenses $F_1$ to $F_N$ of the optical fiber lens array 42 and detected by photoelectric conversion elements $P_1'$ to $P_N'$. Directivity is increased as a numerical aperture NA of each optical fiber lens is reduced.

FIG. 3B illustrates an optical element employing a lens 44. The lens 44 is not restricted to a single one but a plurality of such lenses may be combined with each other. The lens 44 is so arranged that a physical plane P on an excitation light beam incident upon an eyeball is conjugated with an image surface P' on a one-dimensional solid-state image pickup device 35. In this case, images of measuring light components generated from respective parts A and B of the physical plane P having different depths are formed on the image surface P' of the one-dimensional solid-state image pickup device 35 as A' and B'.

Also in case of employing the optical element shown in FIG. 3A or 3B, either one of one-dimensional and two-dimensional solid-state image pickup devices can be employed as a photodetector.

In case of employing a two-dimensional solid-state image pickup device and combining the same with spectroscopic means 37 such as an FT, a filter or an AOTF, not only measuring light components generated from eyeball portions having different depths can be simultaneously detected but the position of the eyeball can be observed by monitoring a two-dimensional image by the two-dimensional solid-state image pickup device. In this case, it is possible to make measurement after confirming that the ocular axis enters a state suitable for the measurement with respect to optical axes of excitation and photoreceiving optical systems without separately providing a CCD image pickup device for monitoring.

Figure 4:
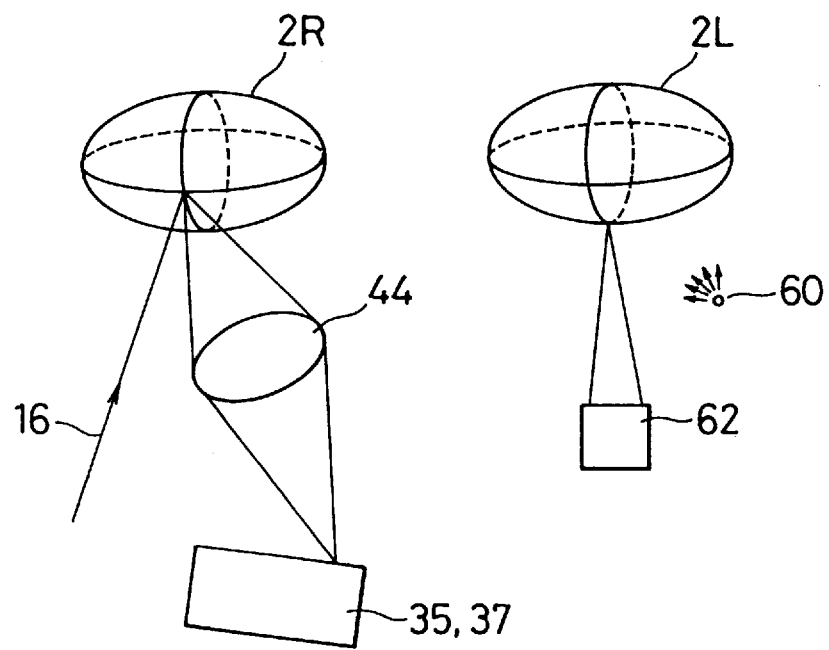
FIG. 4 is a schematic perspective view showing a CCD image pickup apparatus for monitoring provided on the side of a second eyeball which is different from an eyeball for measurement.

FIG. 4 illustrates such an example that a CCD image pickup device for monitoring is provided on another eyeball which is different from that for measurement. It is assumed here that a right eyeball 2R is employed for measurement so that measuring light 16 from an excitation optical system is incident upon this right eyeball 2R, while a photoreceiving optical system comprising a lens 44 and photoreceptors 35 and 37 having spectroscopic means is provided for detecting light from the eyeball 2R.

On the other hand, a left eyeball 2L is provided with a light source 60 for illuminating the eyeball 2L and a CCD image pickup device 62 for monitoring the orientation of the eyeball 2L illuminated with the light source 60 for monitoring the position of the ocular axis.

Figure 5:
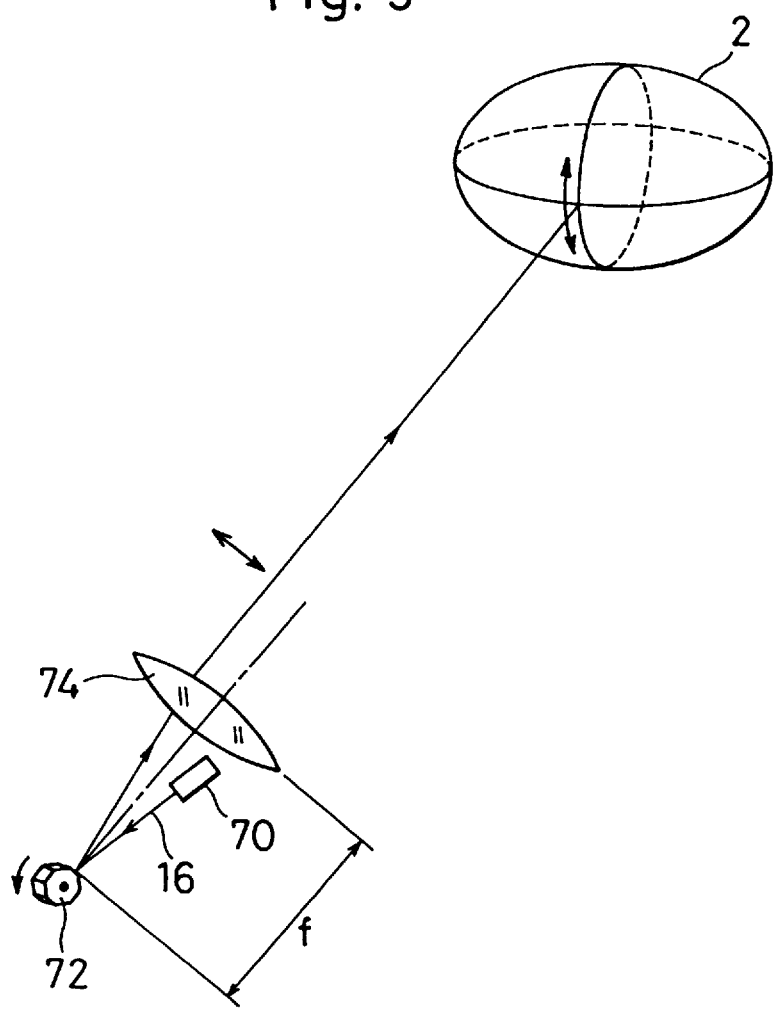
FIG. 5 is a schematic perspective view showing an exemplary excitation optical system comprising a beam sweep mechanism.

FIG. 5 illustrates still another exemplary excitation optical system comprising a beam sweep mechanism for moving an excitation light beam in a direction perpendicular to a plane including optical axes of the excitation optical system and a photoreceiving optical system. In this example, the plane including the optical axes of the excitation and photoreceiving optical systems transversely crosses an eyeball 2, and an excitation light beam 16 is swept in a direction (shown by vertical arrow on the eyeball 2) which is perpendicular to the plane. The excitation optical system is provided with a polygon mirror 72 for sweeping the excitation light beam 16 from a light source 70. A lens 74 is arranged between the polygon mirror 72 and the eyeball 2 so that the polygon mirror 72 is arranged on a focal position of the lens 4, whereby the excitation light beam 16 which is swept by the polygon mirror 72 so that its direction is changed is converted to a parallel beam after passage through the lens 74, and incident upon the eyeball 2 while being swept in the direction shown by arrow on the eyeball 2.

FIGS. 6A, 6B and 6C, illustrating an embodiment integrating the present invention into a goggle structure 50, are a plan view showing arrangement of internal optical systems, a side elevational view on a photoreceiving optical system side showing the arrangement of the internal optical systems, and a perspective view as viewed from an eyeball side respectively. The excitation optical system 12a and the photoreceiving optical system 30 shown in FIG. 2 are arranged in the goggle structure 50. A transmission circuit for driving a light source and a photodetector for transmitting signals detected by the photodetector to the exterior and the like are also provided in the goggle structure 50. A control part 52 includes such a driving part or the transmission circuit.

FIGS. 7 to 14 show exemplary Raman scattering and fluorescence spectra of intraocular substances to be measured in the present invention. In each figure, the excitation light is an He—Ne laser beam of 632.8 nm.

Figure 7:
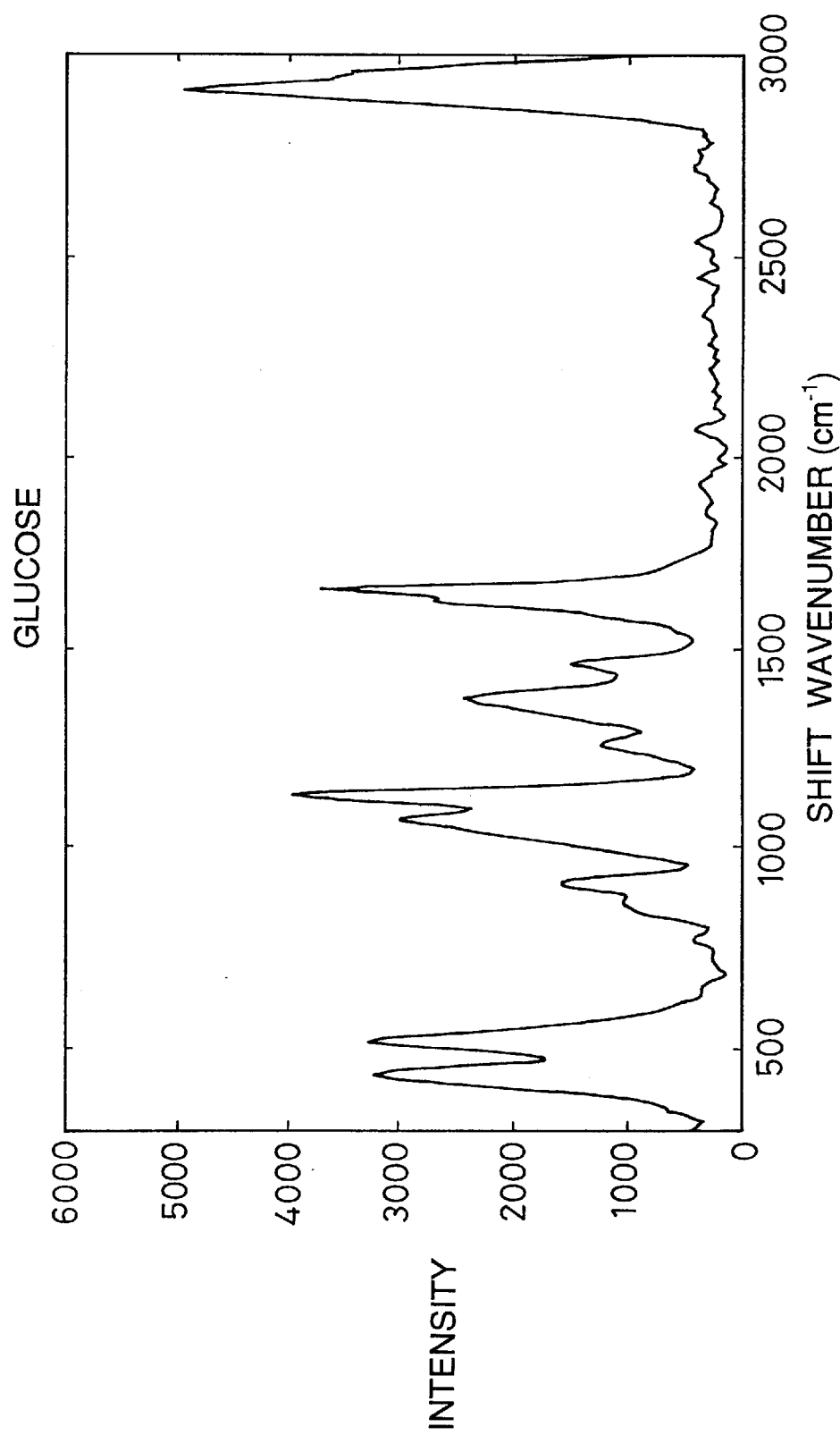
FIG. 7 illu strat es a Raman scattering spectrum of glucose.

FIG. 7 shows a Raman scattering spectrum of glucose, which is provided with peaks at positions of 420 to 450 $cm^{-1}$, 460 to 550 $cm^{-1}$, 750 to 800 $cm^{-1}$, 850 to 940 $cm^{-1}$, 1000 to 1090 $cm^{-1}$, 1090 to 1170 $cm^{-1}$, 1200 to 1300 $cm^{-1}$, 1300 to 1390 $cm^{-1}$, 1400 to 1500 $cm^{-1}$ and 2850 to 3000 $cm^{-1}$ in shift wavenumbers from an excitation wavelength. Central wavenumbers of these peaks are 438 $cm^{-1}$, 530 $cm^{-1}$, 776 $cm^{-1}$, 917 $cm^{-1}$, 1087 $cm^{-1}$, 1103 $cm^{-1}$, 1298 $cm^{-1}$, 1373 $cm^{-1}$, 1461 $cm^{-1}$ and 2907 $cm^{-1}$.

Figure 8:
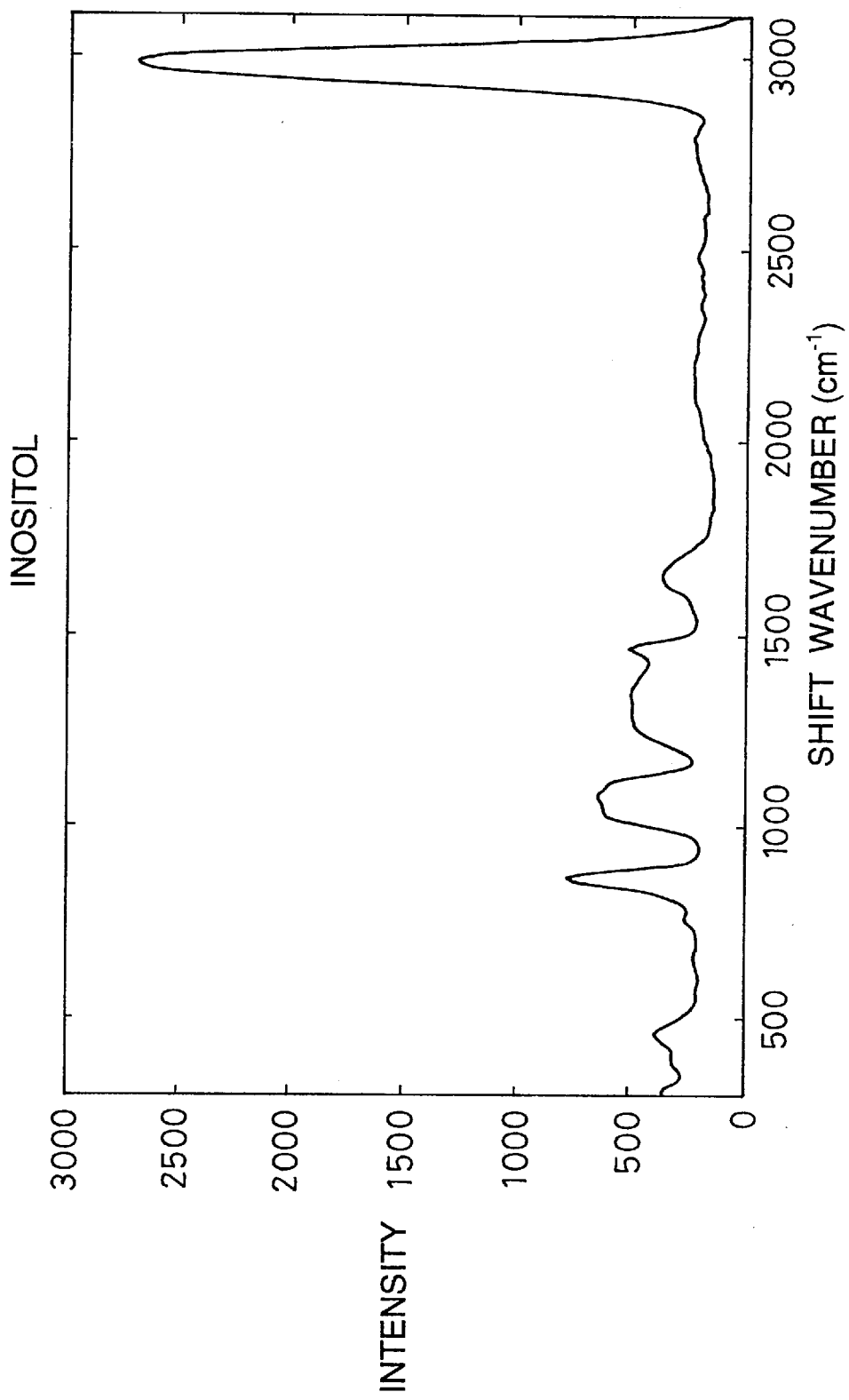
FIG. 8 illustr ates a Raman scattering spectrum of inositol.

FIG. 8 shows a Raman scattering spectrum of inositol, which is provided with peaks at positions of 400 to 500 $cm^{-1}$, 700 to 900 $cm^{-1}$, 1000 to 1100 $cm^{-1}$, 1200 to 1500 $cm^{-1}$ and 2900 to 3050 $cm^{-1}$ in shift wavenumbers from the excitation wavelength. Central wavenumbers of these peaks are 443.852 $cm^{-1}$, 864.743 $cm^{-1}$, 1074.37 $cm^{-1}$, 1468.06 $cm^{-1}$ and 2995.59 $cm^{-1}$.

Figure 9:
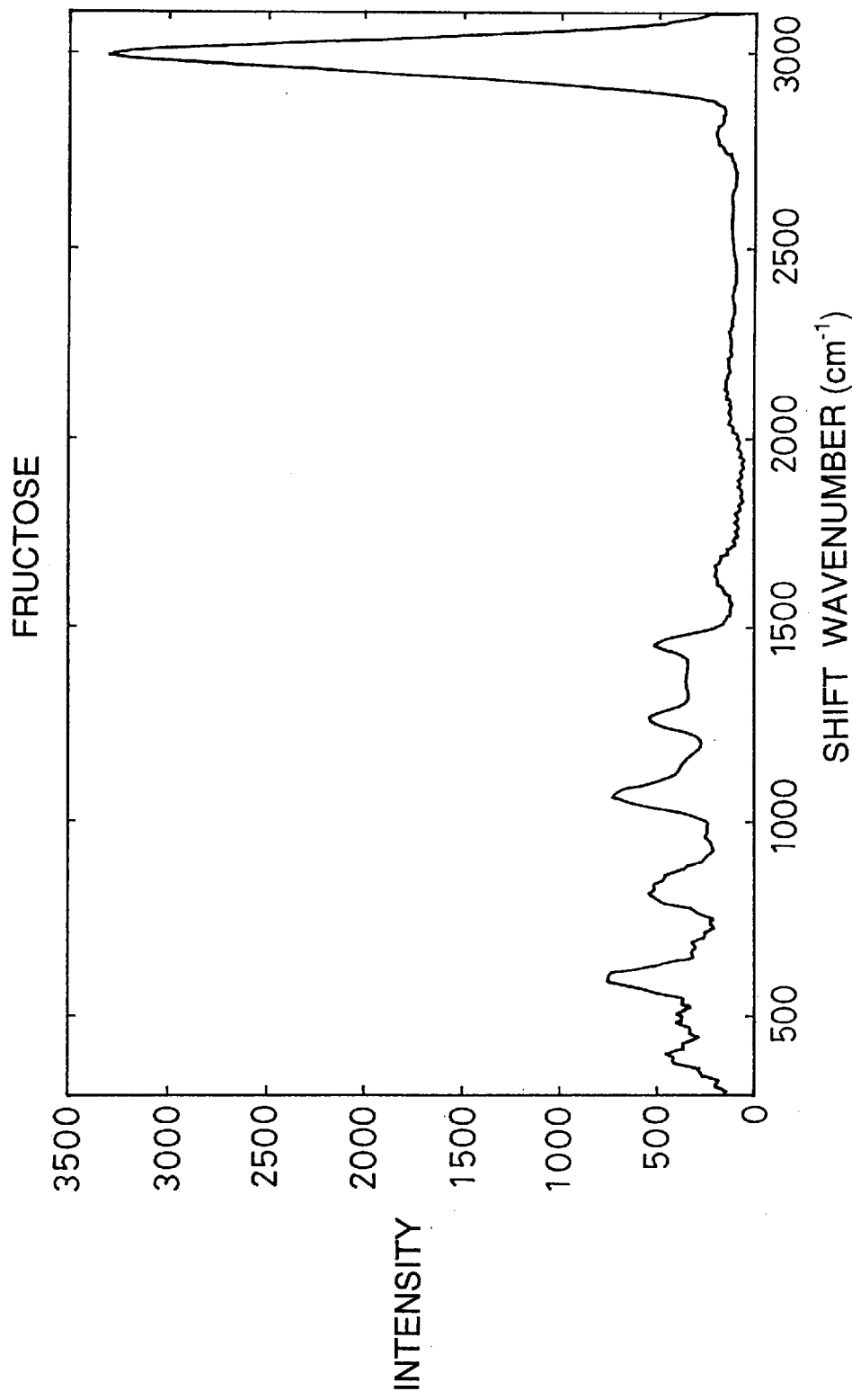
FIG. 9 illustrates a Raman scattering spectrum of fructose.

FIG. 9 shows a Raman scattering spectrum of fructose, which is provided with peaks at positions of 550 to 620 $cm^{-1}$, 650 to 700 $cm^{-1}$, 780 to 870 $cm^{-1}$, 900 to 980 $cm^{-1}$, 1000 to 1150 $cm^{-1}$, 1200 to 1300 $cm^{-1}$, 1400 to 1480 $cm^{-1}$ and 2900 to 3050 $cm^{-1}$ in shift wavenumbers from the excitation wavelength. Central wavenumbers of these peaks are 599.093 $cm^{-1}$, 688.482 $cm^{-1}$, 802. 175 $cm^{-1}$, 963.9821 $cm^{-1}$, 1074.37 $cm^{-1}$, 1267.38 $cm^{-1}$, 1468.0621 $cm^{-1}$ and 2995.59 $cm^{-1}$.

Figure 10:
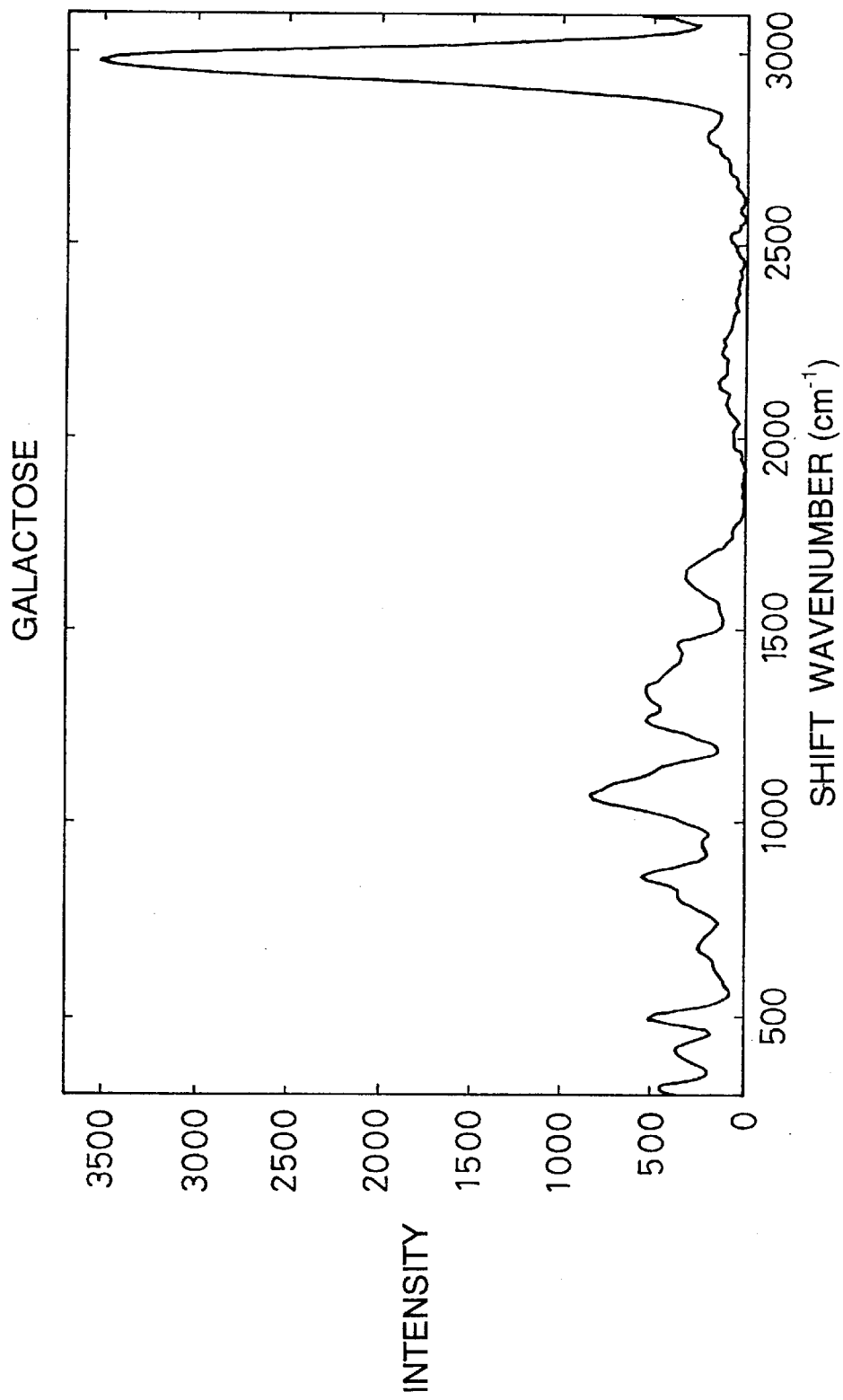
FIG. 10 illustrates a Raman scattering spectrum of galactose.

FIG. 10 shows a Raman scattering spectrum of galactose, which is provided with peaks at positions of 450 to 550 $cm^{-1}$, 630 to 900 $cm^{-1}$, 1000 to 1180 $cm^{-1}$, 1200 to 1290 $cm^{-1}$, 1300 to 1380 $cm^{-1}$, 1400 to 1500 $cm^{-1}$ and 2850 to 3050 $cm^{-1}$ in shift wavenumbers from the excitation wavelength. Central wavenumbers of these peaks are 495.884 $cm^{-1}$, 864.743 $cm^{-1}$, 1062.17 $cm^{-1}$, 1267.38 $cm^{-1}$, 1362.38 $cm^{-1}$, 1468.06 $cm^{-1}$ and 2976.02 $cm^{-1}$.

Figure 11:
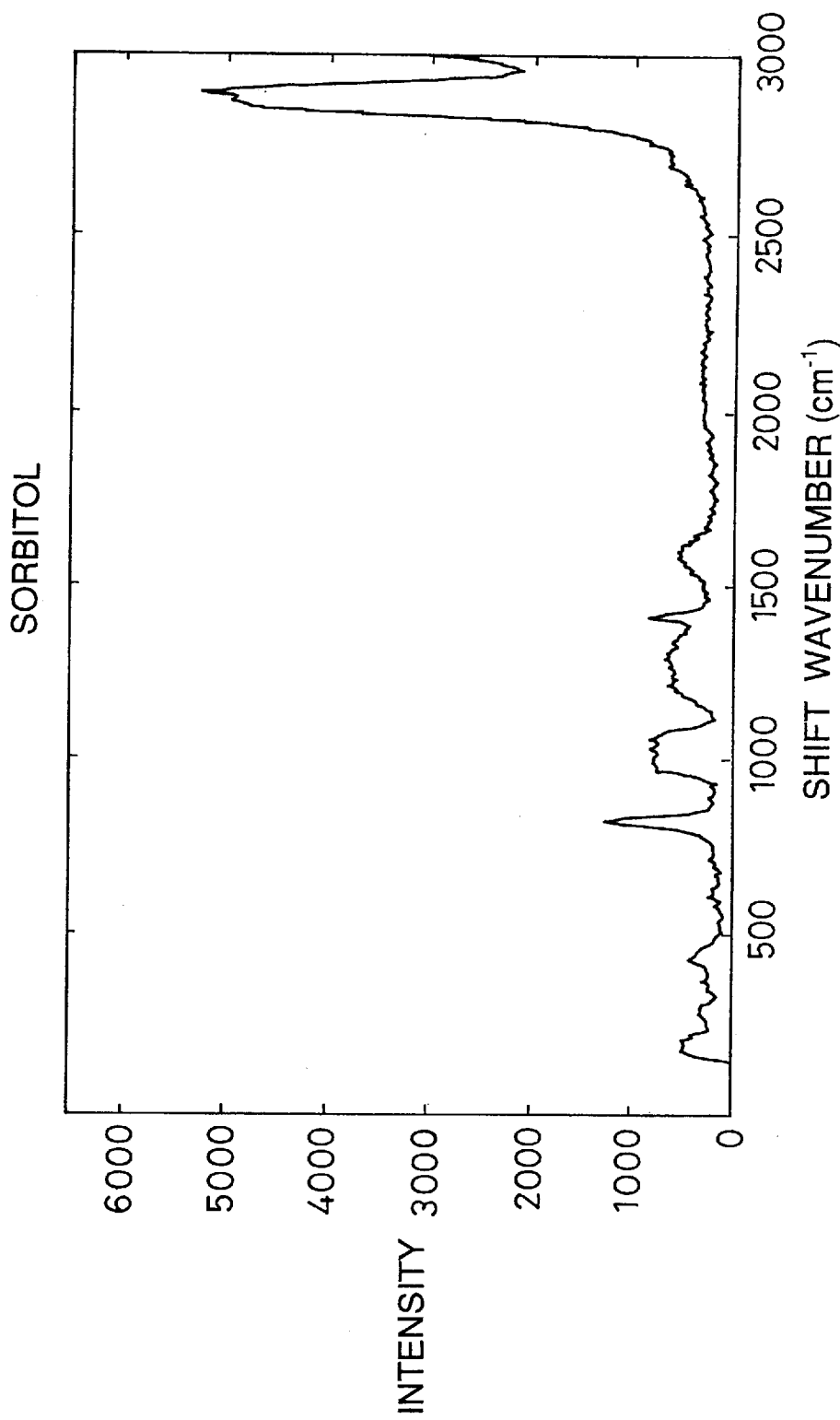
FIG. 11 illustrates a Raman scattering spectrum of sorbitol.

FIG. 11 shows a Raman scattering spectrum of sorbitol, which is provided with peaks at positions of 388 to 488 $cm^{-1}$, 749 to 862 $cm^{-1}$, 933 to 1120 $cm^{-1}$, 1380 to 1464 $cm^{-1}$ and 2731 to 2960 $cm^{-1}$ in shift wavenumbers from the excitation wavelength. Central wavenumbers of these peaks are 438 $cm^{-1}$, 821 $cm^{-1}$, 1414 $cm^{-1}$, nearby 1600 $cm^{-1}$ and 2893 $cm^{-1}$.

Figure 12:
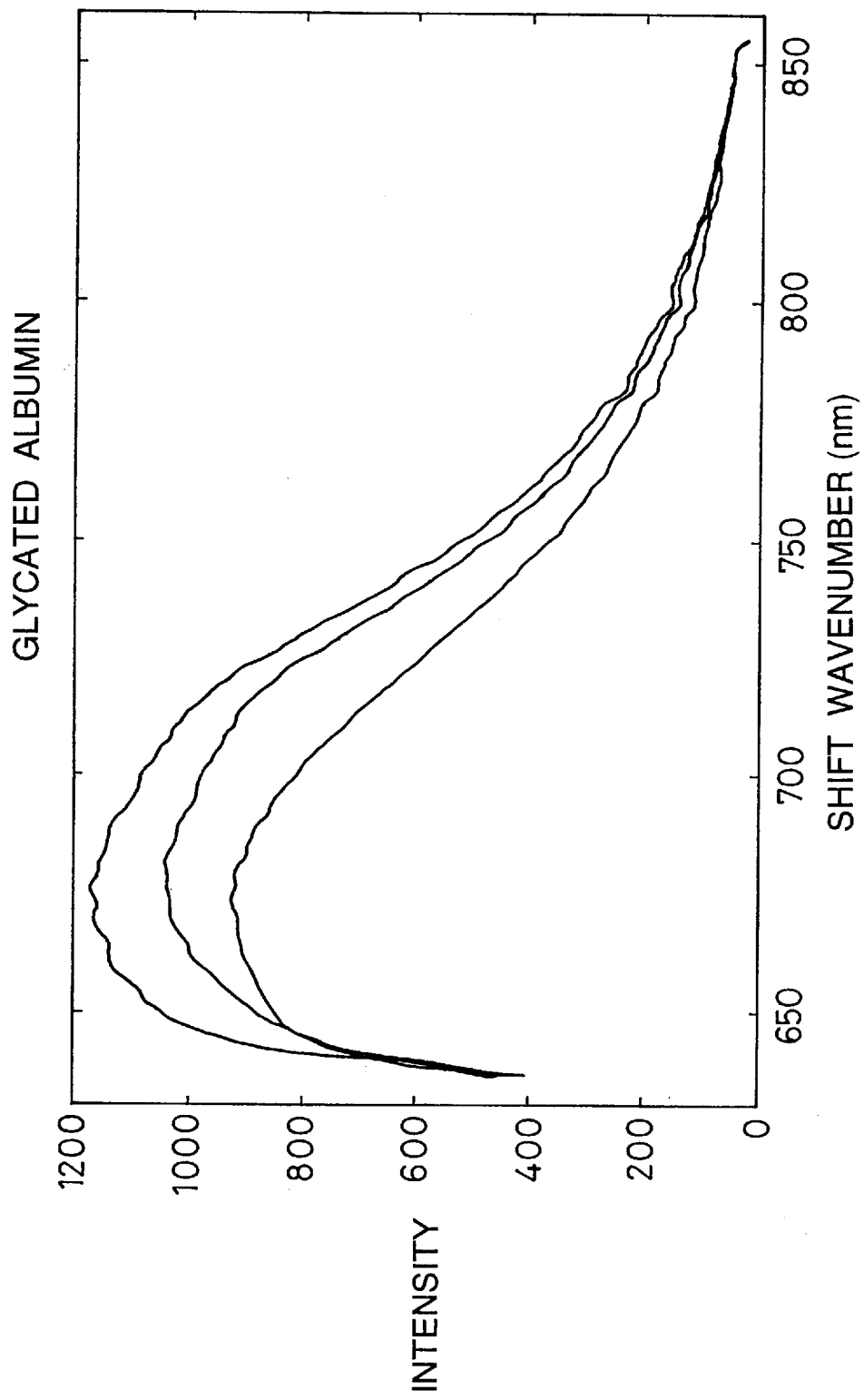
FIG. 12 illustrates a fluorescence spectrum of glycated albumin.

FIG. 12 shows a fluorescence spectra of glycated albumin, which has a peak at 640 to 850 nm. Aqueous solution samples having concentrations of 61.6%, 33.3% and 24.8% are measured, and spectral intensities are increased as the concentrations are increased.

Figure 13:
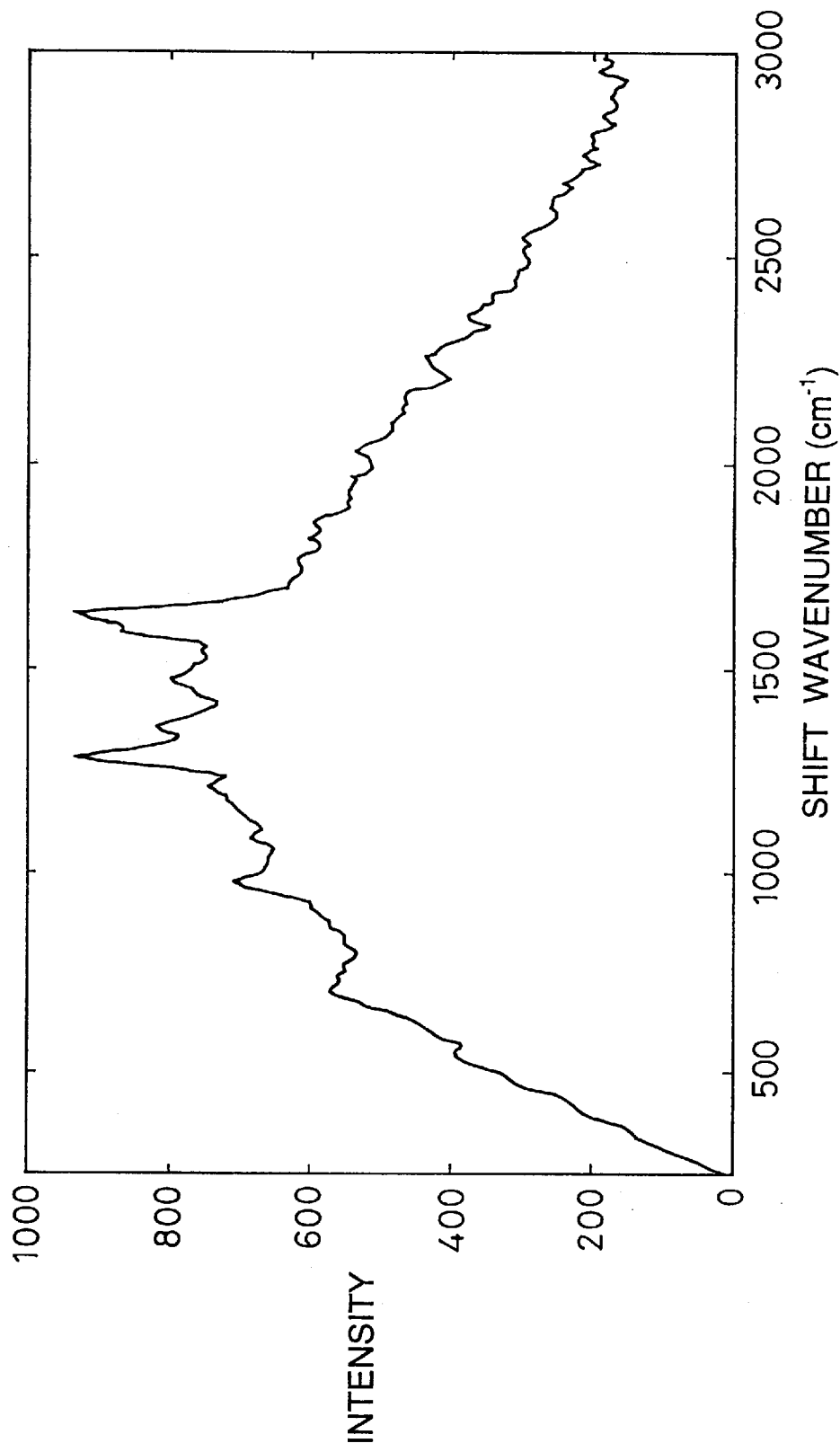
FIG. 13 illustrates a Raman scattering spectrum of ditaurobilirubin.

FIG. 13 shows a Raman scattering spectrum of ditaurobilirubin, which is provided with peaks at positions of 500 to 540 $cm^{-1}$, 670 to 710 $cm^{-1}$, 900 to 980 $cm^{-1}$, 1220 to 1300 $cm^{-1}$, 1310 to 1330 $cm^{-1}$, 1400 to 1500 $cm^{-1}$ and 1550 to 1670 $cm^{-1}$ in shift wavenumbers from an excitation wavelength. Central wavenumbers of these peaks are 520 $cm^{-1}$, 688 $cm^{-1}$, 940 $cm^{-1}$, 1250 $cm^{-1}$, 1320 $cm^{-1}$, 1445 $cm^{-1}$ and 1615 $cm^{-1}$.

Figure 14:
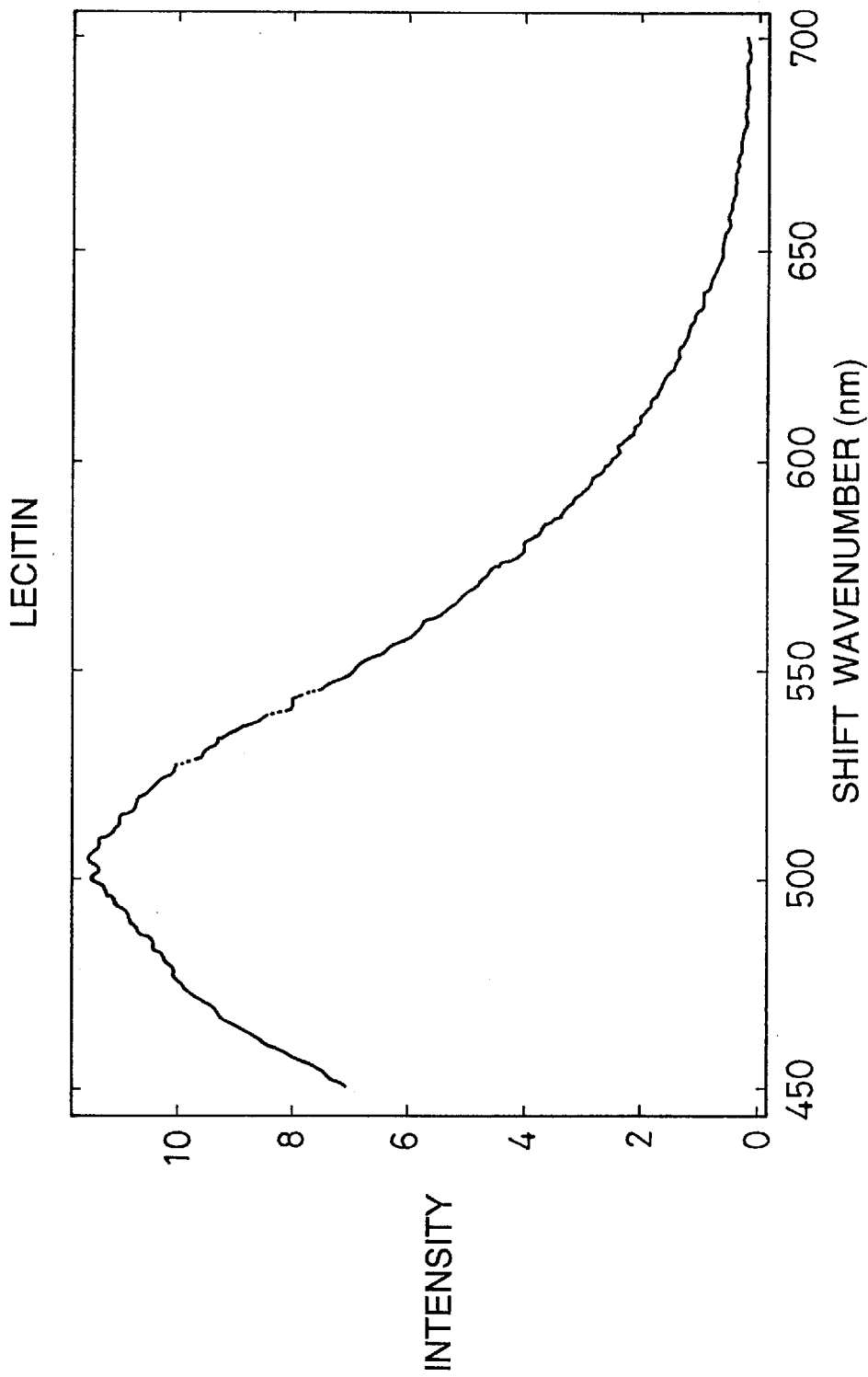
FIG. 14 illustrates a fluorescence spectrum of lecithin.

FIG. 14 shows a fluorescence spectrum of lecithin, which has a peak at 450 to 650 nm.

Although the present invention has been described and illustrated in detail, it is clearly understood that the same is by way of illustration and example only and is not to be taken by way of limitation, the spirit and scope of the present invention being limited only by the terms of the appended claims.

I claim:

1. Apparatus for determining concentration of an intraocular substance in an eyeball, comprising:

an excitation optical system having a monochromated or single-wavelength excitation light beam, wherein said excitation light system is positioned relative to said eyeball so that said excitation light beam is not incident upon an iris in the eyeball, and a photoreceiving optical system having an optical element and a photodetector, wherein the optical element guides a plurality of measuring light components being emitted simultaneously from a plurality of locations within the eyeball, wherein the photodetector is selective for said plurality of measuring light components, wherein each of said measuring light components has spectral intensities, and wherein said concentration ofihe intraocular substance is afinction of said spectral intensities detected by said photodetector.

2. The apparatus in accordance with claim 1, wherein said photoreceiving optical system further comprises a spectroscope to separate said measuring light components being emitted from said eyeball into spectral components, and wherein said photodetector detects said spectral components.

3. The apparatus in accordance with claim 2, wherein said photodetector is a one-dinensional or atwo-dimensional solid-state image pickup device having a plurality of photoelectric conversion elements being arranged along a straight line and forming an angle with an optical axis of said photoreceiving optical system in a plane comprising an optical axis of said excitation optical system and an ocular axis of said photoreceiving optical system, wherein said spectscope is a Fourier transform spectroscope and a filter or an acousto-optic tlmable filter, and wherein said optical element associates positions of said photoelectric conversion elements of said one-dimensional ortwo-dimensional solid-state image pickup device with said plurality of locations within said eyeball.

4. The apparatus in accordance with claim 3, wherein said photodetector is a two-dimensional solid-state image pickup device, and said excitation optical system further comprises a beam sweep mechanism for moving said excitation light beam in a direction being perpendicular to said plane including said optical axes of said excitation and photoreceiving optical systems.

5. The apparatus in accordance with claim 2, wherein said photodetector is a two-dimensional solid-state image pickup device and said spectroscope is a diffraction grating, wherein said optical element associates positions of said photoelectric conversion elements in a series of photoelectric conversion elements in said two-dimensional solid-state image pickup device with said plurality of locations within said eyeball, and said photoreceiving optical system comprises a multichannel spectroscope to disperse said measuring light components in a direction perpendicular to said photoelectric conversion elements in said two-dimensional solid-state image pickup device.

6. The apparatus in accordance with claim 1, being further provided with an ocular axis fixing optical system comprising an ocular axis fixing light source being different from a light source of said excitation optical system, for generating visible light and introducing a light beam from said light source into said eyeball for measent or another eyeball, in order to fix the ocular axis.

7. The apparatus in accordance with claim 1, wherein said photoreceiving optical system comprises a two-dimensional solid-state image pickup device to determine a direction of said eyeball and a position of incidence of said excitation light beam on said eyeball.

8. The apparatus in accordance with claim 1, wherein said photodetector of said photoreceiving optical system is a two-dimensional solid-state image pickup element, being employed also as a monitor for monitoring a direction of said eyeball.

9. The apparatus in accordance with claim 1, wherein said excitation optical system has an optical axis and said photoreceiving optical system has an ocular axis, and wherein the optical axis and the ocular axis intersect on or near a retina of the eyeball.

10. The apparatus in accordance with claim 9, wherein an angle is formed by said optical axis and the ocular axis, and wherein said angle is less than or equal to about 15 degrees.

11. The apparatus in accordance with claim 1, wherein said excitation and photoreceiving optical systems are so arranged that measuring light components that are parallel to said optical axis of said photoreceiving optical system are incident upon said optical element without being blocked by the iris, said measuring light components being generated from said locations of said eyeball having different depths along said excitation light beam from said excitation optical system.

12. The apparatus inaccordancewith claim 1, wherein said optical element is a slit or an optical fiber lens array.

13. The apparatus in accordance with claim 1, wherein said optical element is a conjugate optical system comprising a lens for imaging a set of said measuring light components being emitted from said plurality of locations in said eyeball on said photodetector or said spectroscope.

14. The apparatus in accordance with claim 1, wherein said photodetector is aone dimensional or atwo-dimensional solid-state image pickup device having a plurality of photoelectric conversion elements being arranged along a straight line and forming an angle with an optical axis of said photoreceiving optical system in a plane including optical axes of said excitation and photoreceiving optical systems, and wherein said optical element associates positions of said photoelectric conversion elements of said one-dimensional or two-dimensional solid-state image pickup device with said plurality of locations within said eyeball.

15. The measuring apparatus in accordance with claim 14, wherein said photodetector is a two-dimensional solid-state image pickup device, and said excitation optical system further comprises a beam sweep mechanism for moving said excitation light beam in a direction being perpendicular to said plane including said optical axes of said excitation and photoreceiving optical systems.

16. The apparatus in accordance with claim 1, wherein said excitation optical system comprises a beam splitter, said beam splitter being positioned on an optical axis of said excitation light beam, wherein said beam splitter separates a first portion of said excitation light and wherein said first portion of said excitation light is incident upon a first portion of said photoelectric conversion elements of said photodetector to produce a first output from said photodetector, and wherein an output of a remaining portion of said photoelectric conversion elements receiving said measuring light components from said eyeball is compared to said first output of said photodetector.

17. The apparatus in accordance with claim 1, wherein said excitation and photoreceiving optical systems are housed in a goggle structure being attachable to a face.

18. The apparatus in accordance with claim 17, wherein said goggle structure comprises a transmission circuit for outputting information to an external data processor.

19. The apparatus in accordance with claim 1, wherein said intraocular substance is a sugar, wherein said sugar is glucose, inositol fructose, galactose, or sorbitol and wherein determination is performed with respect to glucose through a Raman scattering peak at 420 to 1500 $cm^{-1}$ or 2850 to 3000 $cm^{-1}$ in a shift wavenumber from an excitation wavelength;

determination is performed with respect to inositol through a Raman scattering peak at 400 to 1500 $cm^{-1}$ or 2900 to 3050 $cm^{-1}$ in a shift wavenumber from said excitation wavelength;

determination is performed with respect to fructose through a Raman scattering peak at 550 to 1500 $cm^{-1}$ or 2900 to 3050 $cm^{-1}$ in a shift wavenumber from said excitation wavelength;

determination is performed with respect to galactose through a Raman scattering peak at 400 to 1500 or 2850 to 3050 $cm^{-1}$ in a shift wavenumber from said excitation wavelength;

determination is performed with respect to sorbitol through a Raman scattering peak at 380 to 1500 $cm^{-1}$ or 2700 to 2960 $cm^{-1}$ in a shift wavenumber from said excitation wavelength.

20. The apparatus in accordance with claim 1, wherein said intraocular substance is a lipid, and determination is performed with respect to lecithin through a spectral intensity of a fluorescence spectrum in a wavelength range of 450 to 650 nm or an integrated value of a spectrum of a proper wavelength range within the range.

21. The apparatus in accordance with claim 1, wherein said intraocular substance is bilirubin, and determination is performed through a Raman scattering peak at 500 to 540 $cm^{-1}$, 670 to 710 $cm^{-1}$, 900 to 980 $cm^{-1}$, 1220 to 1300 $cm^{-1}$, 1310 to 1330 $cm^{-1}$, 1400 to 1500 $cm^{-1}$ or 1550 to 1670 $cm^{-1}$ in a shift wavenumber from an excitation wavelength.

22. The apparatus in accordance with claim 1, wherein said intraocular substance is a glycated protein, and wherein determination is performed with respect to a glycated albumin through a spectral intensity of a fluorescence spectrum in a wavelength range of 640 or 850 nm or an integrated value of a spectrum of a proper wavelength range within the range.

23. The apparatus in accordance with claim 1, wherein said intraocular substance is an advanced glycated end product.

24. The apparatus in accordance with claim 1, wherein said intraocular substance is a glycated crystallin.

25. The apparatus in accordance with claim 1, wherein concentrations of at least two intraocular subtances are measured said substances being a sugar, a lipid, bilirubin or a glycated protein, wherein peak intensities or peak areas of Raman scattered light of shift wavenumbers are selected for said intraocular substances, and wherein spectral intensities of fluorescence or integrated values of wavelength ranges are employed, so that measured values of said substances are obtained from a plurality of values by multivariate regression analysis.

26. The apparatus in accordance with claim 1, wherein said intraocular substance is an exogenous fluorescent substance.

27. The apparatus in accordance with claim 1, wherein said intraocular substance is a sugar, said sugar being glucose, inositol, fructose, galactose, or sorbitol, and wherein determination is performed with respect to glucose through a Raman scattering peak at 420 to 450 $cm^{-1}$, 460 to 550 $cm^{-1}$, 750 to 800 $cm^{-1}$, 850 to 940 $cm^{-1}$, 1000 to 1090 $cm^{-1}$, 1090 to 1170 $cm^{-1}$, 1200 to 1300 $cm^{-1}$, 1300 to 1390 $cm^{-1}$, 1450 to 1500 $cm^{-1}$ or 2850 to 3000 $cm^{-1}$ in a shift wavenumber from an excitation wavelength;

determination is performed with respect to inositol through a Raman scattering peak at 400 to 500 $cm^{-1}$, 700 to 900 $cm^{-1}$, 1000 to 1100 $cm^{-1}$, 1200 to 1500 $cm^{-1}$ or 2900 to 3050 $cm^{-1}$ in a shift wavenumber from said excitation wavelength;

determination is performed with respect to fructose through a Raman scattering peak at 550 to 620 $cm^{-1}$, 650 to 700 $cm^{-1}$, 780 to 870 $cm^{-1}$, 900 to 980$cm^{-1}$, 1000 to 1150 $cm^{-1}$, 1200 to 1300 $cm^{-1}$, 1400 to 1480 $cm^{-1}$ or 2900 to 3050 $cm^{-1}$ in a shift wavenumber from said excitation wavelength;

determination is performed with respect to galactose through a Rarnan scattering peak at 450 to 550 $cm^{-1}$, 630 to 900 $cm^{-1}$, 1000 to 1180 $cm^{-1}$, 1200 to 1290 $cm^{-1}$, 1300 to 1380 $cm^{-1}$, 1400 to 1500 $cm^{-1}$ or 2850 to 3050 $cm^{-1}$ in a shift wavenumber from said excitation wavelength; or determination is performed with respect to sorbitol through a Raman scattering peak at 388 to 488 $cm^{-1}$, 749 to 862 $cm^{-1}$, 933 to 1120 $cm^{-1}$, 1380 to 1464 $cm^{-1}$ or 2731 to 2960 $cm^{-1}$ in a shift wavenumber from said excitation wavelength.

28. Apparatus for determining concentration of an intraocular substance in an eyeball that has an ocular as a function of intensities of spectral components of light emanating from the eyeball, said apparatus comprising:

a monochronated light source that is positionable adjacent an eyeball in a manner that propagates a monochromatic light beam into the eyeball along a first optical axis that is oriented at an angle to said ocular axis such that said first optical axis and said ocular axis are not congruent with each other, a photodectorpositionable adjacent the eyeball and having a plurality of photoelectric elements that are capable of producing singal indicatives of intensity of light that is incident on said photoelectric elements, said photoelectric elements being positioned in a spaced array extending perpendicular to a second optical axis such that said second optical axis extends into the eyeball to intersect said first optical axis, said second optical axis also being at an angle to said ocular axis and in a common plane that includes said first optical axis and said ocular axis such that said ocular axis is positioned between said first optical axis and said second optical axis, said array of photoelectric elements also being positioned in said plane and having a pitch;

a plurality of optical guiide elements positionable in a spaced array between the photodetector and the eyeball on said second optical axis, parallel to said array of photoelectric elements, and with a pitch that matches the pitch of the photoelectric elements such that each optical guide element is positioned to direct light emanating from the eyeball parallel to the second optical axis into one of said photoelectric elements; and a spectroscope positionable on said second optical axis between the photodetector and the eyeball said spectroscope being capable of separating said light emanating from the eyeball into spectral components such that signals produced by said photoelectric elements are indicative of intensities of spectral components of light emanating from the eyeball.

29. A method for determining concentration of a substance in a body of a subject, said method comprising:

(a) irradiating an eye of the subject with an excitation light beam, said excitation light beam being incident upon a plurality of locations within an anterior portion of the eye and reemerging from the eye as a plurality of measuring light components;

(b) passing said plurity of measuring light components through an optical element to guide each of said measuring light components to a corresponding position on a photodetector;

(c) measuring a spectral intensity of each of the measuring light components passing through the optical element and producing electrical signals representative of said measured intensity; and (d) calculating the concentration of the substance based on the measured electrical signals.

30. The method of claim 29, wherein said excitation light beam is a monochromated or single-wavelength light beam.

31. The method of claim 29, wherein said excitation light beam comprises visible or near infrared light.

32. The method of claim 29, wherein said irradiating includes focusing the excitation light beam on the plurality of locations within the eye, wherein the plurality of locations are positioned on an optical axis through the anterior portion of the eye, and wherein the optical axis is not incident upon an iris.

33. The method of claim 29, wherein said optical element is a slit or an optical fiber lens array.

34. The method of claim 29, wherein said passing includes the step of traversing a plurality of thin plates, wherein each of said plates is positioned in an orientation parallel to an optical axis of said plurality of measuring light components.

35. The method of claim 29, wherein said passing includes the step of traversing an array of optical fiber lens, wherein each of said optical fiber lens is positioned in an orientation parallel to an optical axis of said plurality of measuring light components.

36. The method of claim 29, wherein said optical element is a conjugate optical system comprising a lens, wherein said lens images said measuring light components being emitted from said plurality of locations with said eye onto a photodetector.

37. The method of claim 29, wherein said measuring light components are scattered light or fluorescence.

38. The method of claim 29, further comprising separating said measuring light components into spectral components before measuring a special intensity.

39. The method of claim 38, wherein said step of separating includes the step of passing said measuring light components through a spectroscope.

40. The method of claim 39, wherein said spectroscope is a courier transform spectroscope, a filter, or an acousto-optic tunable filter.

41. The method of claim 29, wherein said irradiating includes splitting the excitation light beam into a first portion and a second portion, said first portion being incident upon a photodetector and said second portion being incident upon the eye.

42. The method of claim 41, wherein said step of splitting the excitation light beam is performed using a half mirror positioned between an excitation light source and the eye.

43. The method of claim 29, further comprising stabilizing an ocular axis of a photoreceiving optical system, said photoreceiving optical system comprising the optical element and the photodetector.

44. The method of claim 43, wherein the stabilizing includes exposing the eye to visible light to stabilize the ocular axis between the eye and the photodetector by generating a beam of visible light, passing the beam of visible light through a slit to produce a narrow beam of light, focusing the narrow beam of light on a half mirror, and reflecting a portion of the narrow beam of light into the eye.

45. The method of claim 29, wherein said substance is a sugar, a lipid, bilirubin or a glycated protein.

46. The method of claim 29, wherein said photodetector is a one-dimensional or a two-dimensional solid-state image pickup device having aplurality of photoelectric conversion elements.

* * * * *